US010695122B2

(12) United States Patent
Gonzalez-Martinez et al.

(10) Patent No.: US 10,695,122 B2
(45) Date of Patent: Jun. 30, 2020

(54) SYSTEMS AND METHODS FOR CREATING ONE OR MORE LESIONS IN NEUROLOGICAL TISSUE

(71) Applicant: THE CLEVELAND CLINIC FOUNDATION, Cleveland, OH (US)

(72) Inventors: Jorge Gonzalez-Martinez, University Heights, OH (US); Imad Najm, Cleveland, OH (US); John T. Gale, Chardon, OH (US); Karl West, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 102 days.

(21) Appl. No.: 15/790,466

(22) Filed: Oct. 23, 2017

(65) Prior Publication Data

US 2018/0110558 A1    Apr. 26, 2018

Related U.S. Application Data

(60) Provisional application No. 62/411,880, filed on Oct. 24, 2016.

(51) Int. Cl.
*A61B 18/20* (2006.01)
*A61B 18/14* (2006.01)
(Continued)

(52) U.S. Cl.
CPC .......... *A61B 18/14* (2013.01); *A61B 18/1492* (2013.01); *A61B 18/20* (2013.01);
(Continued)

(58) Field of Classification Search
CPC .......... A61B 18/00; A61B 2018/00005; A61B 2018/00315; A61B 2018/0039;
(Continued)

(56) References Cited

U.S. PATENT DOCUMENTS 6,463,317 B1 * 10/2002 Kucharczyk ....... A61B 5/02014
                                                  600/411
6,497,699 B1 * 12/2002 Ludvig ............. A61M 5/14276
                                                  604/67
(Continued)

FOREIGN PATENT DOCUMENTS

WO    2015/148470 A1    10/2015

OTHER PUBLICATIONS

PCT International Search Report and Written Opinion for corresponding PCT Application No. PCT/US2017/057882, dated Jan. 23, 2018, pp. 1-17.

*Primary Examiner* — Ahmed M Farah
(74) *Attorney, Agent, or Firm* — Tarolli, Sundheim, Covell & Tummino LLP

(57) ABSTRACT

This disclosure relates to forming a lesion in a patient's neurological tissue without requiring general anesthesia. The lesion can be either temporary or permanent. In either case, the lesion can be created by a steerable probe that includes a steerable guide, a laser device, and at least one electrode. The steerable guide steers the probe to a target location in the subject's neurological tissue. When the probe reaches the target location, the laser can create the lesion. The at least one electrode can detect a progressive vanishing of neural activity from the portion of the neurological tissue due to the lesion.

7 Claims, 8 Drawing Sheets

(51) Int. Cl.
  *A61B 18/24* (2006.01)
  *A61N 1/05* (2006.01)
  *A61B 18/00* (2006.01)
  *A61B 17/00* (2006.01)
  *A61B 18/08* (2006.01)

(52) U.S. Cl.
  CPC ............ *A61B 18/24* (2013.01); *A61N 1/0502* (2013.01); *A61B 18/082* (2013.01); *A61B 2017/00053* (2013.01); *A61B 2017/00128* (2013.01); *A61B 2018/00005* (2013.01); *A61B 2018/0022* (2013.01); *A61B 2018/0044* (2013.01); *A61B 2018/0066* (2013.01); *A61B 2018/00434* (2013.01); *A61B 2018/00446* (2013.01); *A61B 2018/00577* (2013.01); *A61B 2018/00642* (2013.01); *A61B 2018/00666* (2013.01); *A61B 2018/00696* (2013.01); *A61B 2018/00839* (2013.01); *A61B 2018/00875* (2013.01); *A61B 2018/00964* (2013.01)

(58) Field of Classification Search
  CPC .. A61B 2018/00434; A61B 2018/0044; A61B 2018/00446; A61B 2018/00577; A61B 2018/00636; A61B 2018/00642; A61B 18/18; A61B 2018/1869; A61B 18/20; A61B 2018/2005; A61B 18/22; A61B 2018/2255; A61B 18/24; A61B 18/28; A61B 18/04; A61B 18/08; A61B 18/082; A61B 18/14; A61B 18/1402; A61B 18/142; A61B 18/1492; A61B 34/10; A61B 34/101; A61B 34/1002; A61B 2034/108; A61N 5/06; A61N 5/0601; A61N 5/0613; A61N 5/0618; A61N 5/0622; A61N 2005/0643; A61N 2005/067; A61N 1/04; A61N 1/05; A61N 1/0504; A61N 1/0529; A61N 1/0551

USPC ............ 606/10–16; 607/88, 89, 92, 115–118
  See application file for complete search history.

(56) References Cited

U.S. PATENT DOCUMENTS

| | | | |
|---|---|---|---|
| 6,575,969 B1 | 6/2003 | Rittman, III et al. | |
| 7,853,303 B2 | 12/2010 | Nikumb et al. | |
| 8,242,409 B2* | 8/2012 | Prabhu | A61F 2/82 219/121.72 |
| 8,391,957 B2* | 3/2013 | Carlson | A61M 25/0662 600/429 |
| 2013/0035681 A1 | 2/2013 | Subramaniam et al. | |
| 2013/0085631 A1 | 4/2013 | Mercanzini et al. | |
| 2013/0172869 A1* | 7/2013 | Bonfeld | A61N 1/3706 606/33 |
| 2013/0274614 A1 | 10/2013 | Shimada et al. | |
| 2015/0265348 A1* | 9/2015 | Avitall | A61B 5/044 606/34 |
| 2016/0022353 A1 | 1/2016 | Forsyth et al. | |
| 2016/0051806 A1* | 2/2016 | Goldsmith | A61N 1/00 604/21 |
| 2018/0028807 A1* | 2/2018 | Gonzalez-Martinez | A61N 1/08 |
| 2018/0103848 A1* | 4/2018 | Kinser | A61N 5/0601 |
| 2019/0374213 A1* | 12/2019 | Goldsmith | A61B 10/02 |

\* cited by examiner

SYSTEMS AND METHODS FOR CREATING ONE OR MORE LESIONS IN NEUROLOGICAL TISSUE

CROSS-REFERENCE TO RELATED APPLICATIONS

This application claims the benefit of U.S. Provisional Application No. 62/411,880, entitled "SYSTEMS AND METHODS FOR CREATING LESIONS IN NEUROLOGICAL TISSUE," filed 24 Oct. 2016. The entirety of this provisional application is hereby incorporated by reference for all purposes.

TECHNICAL FIELD

The present disclosure relates generally to creating one or more lesions in neurological tissue and, more specifically, to systems and methods that employ a steerable probe for the controlled creation of lesions in neurological tissue.

BACKGROUND

Epilepsy is among the most common disorders of the nervous system, affecting as many as 50 million people worldwide. As many as 30% of the people with epilepsy as characterized as having medically refractory epilepsy (MRE). Patients with MRE suffer from a particularly challenging form of epilepsy that is not responsive or minimally responsive to anti-epileptic drugs. A range of surgical interventions are possible for MRE, all of which rely on the precise localization of epileptogenic foci within the brain. However, some patients require multiple surgical interventions, resulting in high morbidity and relatively low efficacy (approximately 50% of the patients who undergo invasive monitoring for epilepsy will fail the surgical treatment). Many of these patients will not even be considered candidates for conventional surgery due to the extent and complexity of the epileptic areas. In addition, many other neurological disorders continue to have poor outcomes despite management with invasive or noninvasive therapies. These include brain tumor, chronic pain conditions (e.g., neuropathic pain, cancer related pain, and the like), and movement disorders (e.g., Parkinson's disease, essential tremor, symptomatic tremors, and other movement problems).

SUMMARY

The present disclosure relates generally to creating one or more lesions in neurological tissue and, more specifically, to systems and methods that employ a steerable probe for the controlled creation of lesions in neurological tissue. The lesion in the neurological tissue (e.g., the brain, spinal cord, peripheral nerve, etc.) can treat a neurological condition. In some instances, the lesion can be a permanent lesion. In other instances, the lesion can be temporary in advance of a permanent ablation.

In one aspect, the present disclosure includes a system that creates a lesion in portion of neurological tissue. The system includes a probe configured to be implanted within a subject's neurological tissue. The probe includes: a laser device; an electrode including at least one electrode contact configured for recording (in some instances, the at least one electrode can also be configured for stimulation); and a steerable device. The system also includes a computing device coupled to the probe. The computing device includes a non-transitory memory storing instructions; and a processor configured to access the non-transitory memory and execute the instructions to: guide the probe to a predetermined location within the subject's neurological tissue using the steerable device; deliver a signal to the laser device that causes the laser device to form a lesion in the associated predetermined location; and receive a feedback signal related to the lesion from the at least one electrode contact.

In another aspect, the present disclosure includes a method for controlling the creation of a lesion in neurological tissue. The method can be executed by a system that includes a processor. A probe can be steered or guised to a predefined location in a subject's neural tissue using a steerable guide device. The probe includes the steerable guide device, a laser device, and an electrode with at least one electrode contact configured for recording and/or stimulation. A signal can be sent instructing the laser to form a lesion within in the predefined location. In response to the creation of the lesion, a feedback signal can be received from the at least one electrode contact. The feedback signal includes electrical conduction information related to development of the lesion.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
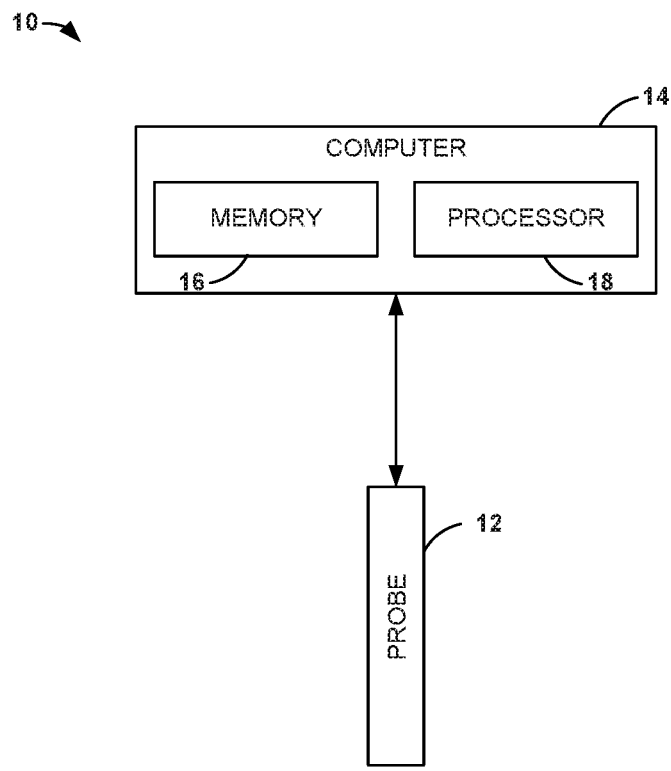
FIG. 1 is diagram of a system that can be used to create at least one lesion in a patient's neural tissue to treat a neurological condition in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "probe" can refer to a medical instrument used for exploring a part of the body. In some instances, the probe can have a blunt end.

As used herein, the term "steerable hybrid catheter (SHC)" can refer to a type of probe that includes a laser for creating a lesion, at least one electrode to provide feedback about the lesion, and a steerable guide device to guide the SHC device to the portion of neurological tissue to create the lesion. Although the SHC can be embodied as a catheter, any type of probe that can accommodate the laser, the at least one electrode, and the steerable guide is included under the term SHC.

As used herein, the term "laser" can refer to a device that can deliver ablative energy to a portion of neural tissue, which can lead to the formation of a lesion in the portion of neural tissue. For example, the laser can provide current, heat, and/or light to the portion of neural tissue.

As used herein, the term "lesion" can refer to a region in an organ or tissue (e.g., a portion of the nervous system) that has suffered damage through injury. In some instances, the lesion can be caused by a current (from the laser) that can burn the tissue to create the lesion. In other instances, the lesion can be caused by a laser that shines light to burn the tissue to create the lesion. A lesion is formed by the laser during a process referred to as "ablation".

As used herein, the term "electrode" can refer to a device that includes at least one "electrode contact". The electrode can include an insulation material surrounding the at least one electrode contact. It will be understood that the term "electrode" can be used herein to describe a grouping of one or more stimulating and/or recording contacts.

As used herein, the term "electrode contact" can refer to a conductor that can establish an electrical connection with at least a portion of a patient's body, such as neural tissue. The electrical connection can be used for stimulating (e.g., including delivering an ablating current to the portion of the patient's body to create a lesion). However, the electrical connection can also be used for recording applications. Electrode contacts can be constructed of different conductive materials, in different shapes, in different sizes, or the like.

As used herein, the terms "steerable device" and "steerable guide device" can be used interchangeably to refer to a device (e.g., a guidewire and/or an inflatable balloon) that can guide the SHC for placement in the body.

As used herein, the term "nervous system" can refer to at least a portion of the brain, the spinal cord, and/or the peripheral nervous system.

As used herein, the term "neurological condition" can refer to a disorder of the nervous system resulting from an abnormality (e.g., biochemical, structural, and/or electrical). Examples of neurological conditions can include epilepsy, brain tumor, movement disorder, chronic pain, cancer pain, a psychiatric disorder, or the like.

As used herein, the terms "neural tissue" and "neurological tissue" can refer to any organs, cells, or tissue in the nervous system. Examples can include central nervous system tissue (brain or spinal cord) and/or peripheral nervous system tissue (motor neurons, sensory neurons, autonomic neurons).

As used herein, the term "abnormal neurological activity" can refer to anomalous electrical conduction in at least a portion of the nervous system (e.g., brain, spinal cord, peripheral nervous system) that can be exhibited by a neurological condition.

As used herein, the term "zone of activity" can refer to a neural network that includes nodes that are responsible for the generation and/or propagation of the abnormal neural activity. In some instances, the zone of activity can refer to an epileptogenic zone (EZ) that includes nodes within a specific neural network responsible for the generation of the abnormal neural activity. For example, the EZ may include the focus or foci of a seizure.

As used herein, the terms "target area" and "theoretical zone of activity" can refer to an area corresponding to an initial estimate of a suspected zone of activity of a neurological condition based on pre-operative non-invasive data. A thermo-coupled multi-contact electrode can be implanted to a specific location in the target area to determine the actual zone of activity.

As used herein, the term "conduction data" can refer to data included in signals recorded by one or more contacts of the thermo-coupled multi-contact electrode. In some instances, the conduction data can be used to construct an electroencephalogram (EEG) showing conduction in at least a portion of the nervous system.

As used herein, the term "stereotactic" can refer to a technique for locating one or more points inside a target area in a patient's brain using an external, three-dimensional frame of reference based on a three-dimensional coordinate system. For example, one or more SHCs can be implanted within a plurality of specific locations in a target area using a stereotactic implantation device.

As used herein, the term "medical professional" can refer to can refer to any person involved in medical care of a patient including, but not limited to, physicians, medical students, nurse practitioners, nurses, and technicians.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to creating one or more lesions in neurological tissue and, more specifically, to systems and methods that employ a steerable probe for the controlled creation of lesions in neurological tissue. The lesions can be used to treat a neurological condition, like certain types of epilepsy, brain tumor, psychiatric disorder, movement disorder, chronic pain, cancer pain, or the like. The one or more lesions can be created in a patient's neural tissue at the patient's bedside without the need for general anesthesia. The lesions can be temporary, allowing for testing of whether the lesion treats the neurological condition. However, alternatively, the lesions can be permanent, permanently treating the neurological condition. The systems and methods described herein can lead to the occurrence of fewer complications and shortened lengths of stay for patients.

The one or more lesions can be created less invasively than other therapy options using a probe, like a steerable hybrid catheter (SHC) device. The SHC device can include a laser device, at least one electrode, and a steerable guide device. The laser device can create a lesion in a portion of neurological tissue. The at least one electrode can detect a progressive vanishing of neural activity from the portion of the neurological tissue due to the lesion. The at least one electrode can provide feedback about the progress of the lesion, which can be used to determine when the lesion is complete. For example, the one or more lesions can be created at the location theorized to be within the portion of the zone of activity that is responsible for a primary organization of the abnormal neural activity. In some instances, the lesion can be temporary to allow for testing of whether the lesion is created in the proper portion of the zone of activity that is responsible for primary organization of the abnormal neural activity.

III. Systems

One aspect of the present disclosure can include a system 10 (FIG. 1) for forming a lesion in a patient's neural tissue (e.g., within the patient's brain, spinal cord, peripheral nervous system, or the like). The lesion can be created less invasively, with far less expense (e.g., monetary, mortality, and/or morbidity, than with other traditional treatment options. During formation of the lesion, a feedback signal can be recorded related to the development of the lesion to ensure that the lesion is fully formed. The goal of the lesion is to treat a neurological condition, such as epilepsy, brain tumor, psychiatric disorder, movement disorder, chronic pain, cancer pain, or the like.

The system 10 can include a probe 12 conductively coupled to a computer 14 (which can include one or more computers). The probe 12 can be configured for implantation within the subject's neurological tissue. The computer 14 can include a non-transitory memory 16 storing instructions and a processor 18 configured to access the non-transitory memory 16 can execute the instructions. The non-transitory memory 16 can be any kind of hardware storage and not a transitory signal, while the processor 18 can be any type of hardware processor (e.g., a microprocessor). The communicative coupling can be wired coupling, wireless coupling, or a combination between wired and wireless coupling. The communicative coupling can allow the computer 14 to control actions undertaken by the probe 12 and/or receive feedback from the probe 12.

Figure 2:
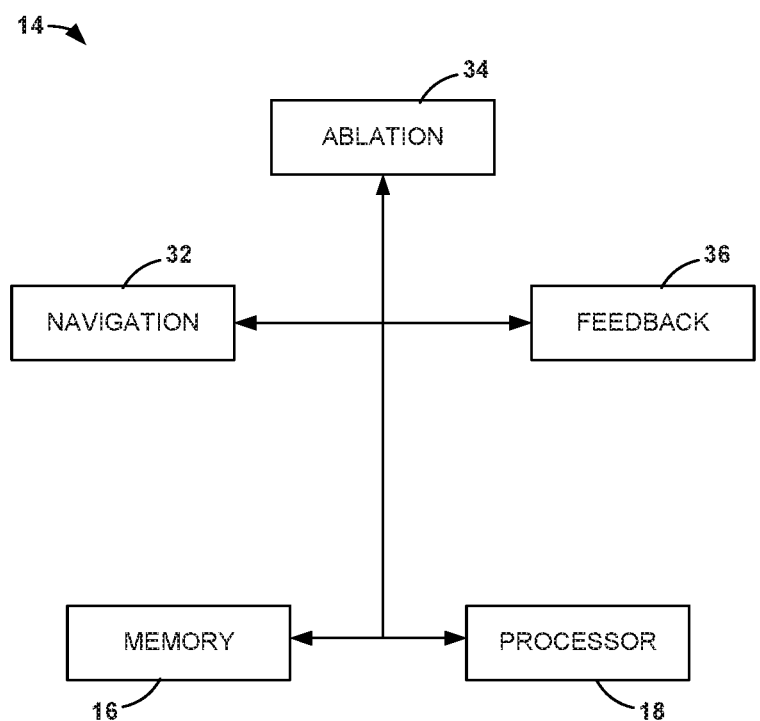
FIG. 2 is a diagram of the computing device of FIG. 1.

The computer 14 is shown in more detail in FIG. 2. The computer can include a non-transitory memory 16, storing data and instructions, coupled to a processor 18, configured to access the non-transitory memory 16 and execute the instructions. For example, the non-transitory memory 16 can store data related to neural networks as previously defined based on pre-operative recording (either noninvasive, like imaging or surface EEG, or invasive, like a stereo-electro-encephalography (SEEG) mapping procedure). The non-transitory memory 16 can also store instructions that are executed by the processor 18 to facilitate performance of operations related to the probe 12. The processor 18 can execute the instructions to perform operations, including navigation 32, ablation 34, and feedback 36. In other words, when performing the operations, the processor 18 can communicate with a bi-directional manner with the probe 12.

When executed, the instructions stored in the non-transitory memory 16 can be directed to various components of the probe 12. The instructions can work together and with the probe 12 to create one or more lesions in one or more target areas of the neural tissue. For example, a navigation 32 instruction can relate to control of movement and position of the probe 12. The ablation 34 instruction can relate to control of the formation of the lesion and the delivery of an ablating energy (e.g., current, light, heat, cooling) to the nearby tissue. The feedback 36 instruction relates to the receipt of a feedback signal from probe 12. When the ablation is deemed to be complete, the probe 12 can be moved to another location, removed from the patient's body, or left in place for a testing period.

Figure 3:
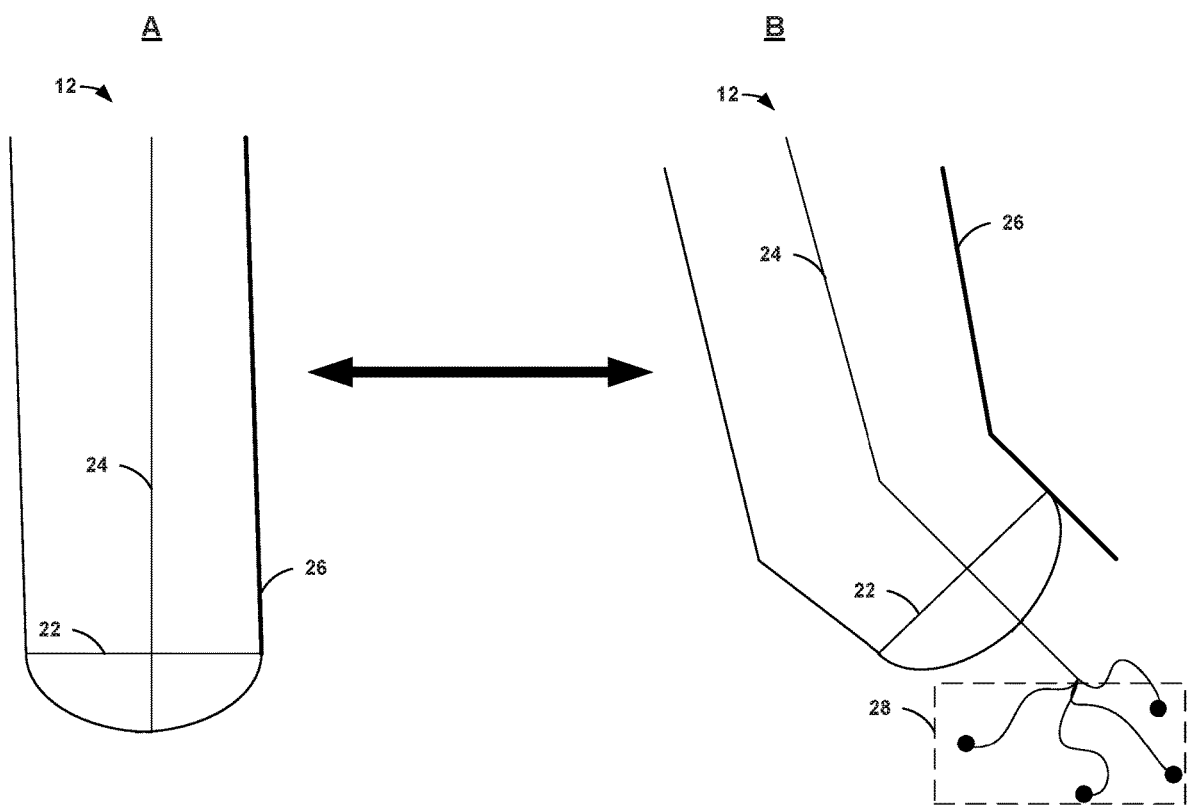
FIG. 3 is a diagram, of the probe of FIG. 1 in different positions.

The operation of the probe 12 in response to the instructions is shown in FIG. 3. In this example, the probe 12 is illustrated as a steerable hybrid catheter (SHC) device, in which a catheter houses a laser device 22 and an electrode 24 (illustrated as an example with four contacts 28). A steerable guide device 26 is insertable into a side port of the catheter. Although not illustrated, each of the laser device 22, the electrode 24, and the steerable guide 26 can be communicatively coupled to the computer 14 of FIG. 2. In some instances, implantation of the probe 12 can be conducted with the aid of a stereotactic device or system.

The laser device 22 can create a lesion at a location in the target area in response to an ablation 34 instruction from the computer 14. The lesion can be created by the application of a pulse of high energy to the target area. In some instances, the pulse of high energy can be electrical energy (e.g., provided through a short current burst). In other instances, the pulse of high energy can be optical energy, heat energy, or cooling energy (e.g., provided through a short high-energy laser burst). In some instances, the lesion can be a permanent lesion. A permanent lesion can stop conduction in the area of the lesion. For example, the permanent lesion can be created by ablating the neural tissue. In other instances, the lesion can be a temporary lesion, which can temporarily cease local nerve activity (e.g., for a time period lasting from minutes to days). The temporary lesion can be fully reversible, so that normal neural activity/conduction can resume at the spot of the temporary lesion. If the temporary lesion does stop the abnormal neural activity, a permanent lesion can be created. However, if the temporary lesion does not stop the abnormal neural activity, the temporary lesion can return to normal and another temporary lesion can be created at a different location. Additionally, the temporary lesion can be evaluated to determine if the temporary lesion causes a deficit (e.g., speech, motor, etc.) in advance of a permanent lesion being created.

The electrode 24 can detect a progressive vanishing of neural activity due to the lesion and send a feedback 38 signal to the computer 14. The feedback signal can include an electrical recording indicative of the progressive vanishing of neural activity in the target region and/or at the location based on the lesion. In other words, the feedback signal can indicate progress of the lesion, which can be used to determine when the lesion is complete. For example, the feedback signal can be an electrical signal related to conduction in the neural tissue as the lesion is being created. When the conduction ceases (or reaches a predetermined level indicating background conduction), the lesion is determined to be complete, for example.

As shown in B, the electrode can extend into the surrounding neural tissue so that one or more electrode contacts 28 (four contacts are illustrated) can expand to different locations within the surrounding neural tissue. In some instances, the electrode contacts 26 can be recording contacts; however, the electrode contacts 26 can also be configured for recording and/or stimulation. For example, a stimulating contact can deliver a stimulation to the portion of neural tissue and the one or more recording contacts can detect the response of the neural tissue to the stimulation. Progress of the lesion can be monitored by the computer 14 based on the resulting feedback 38 signal.

The steerable guide 26 can guide the probe 12 to the precise location within the target area determined by the navigation 32 of the computer 12. The navigation 32 can use coarse navigation to guide the probe 12 into the target area to coarse coordinates indicative of the target area and then fine navigation to guide the probe 12 to the precise location according to fine coordinates corresponding to the location within the coarse coordinates. The target area can be a three-dimensional space and the location can be a point in three dimensions within the space. The steerable guide 28 can move in three dimensions, causing the probe 12 to move in three dimensions (e.g., (x, y, z) in the Cartesian coordinate system, (r, theta, phi) in the spherical coordinate system, etc.). The steerable guide 26 can cause at least a portion of the probe 12 to bend or otherwise change shape to navigate to the target area and/or the location. For example, the steerable guide 26 can be in the form of a guidewire (as shown) and/or an inflatable balloon. In instances where the stereotactic device or system is used, the navigation 32 can also be linked to the stereotactic device or system.

Figure 4:
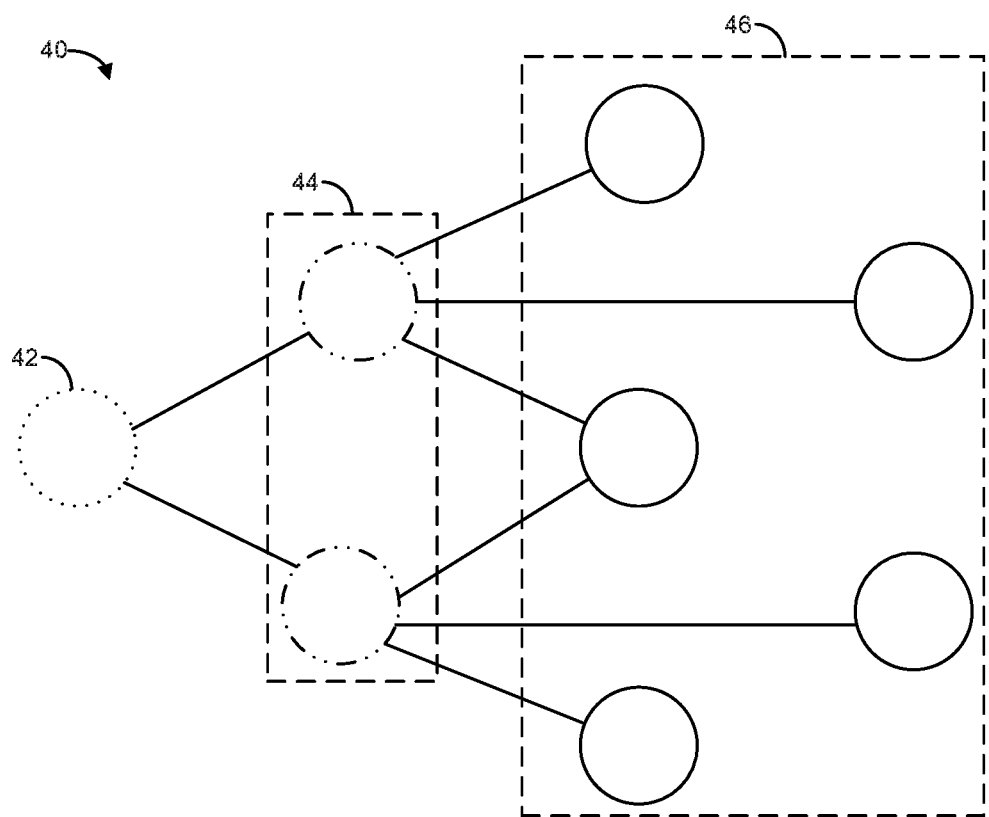
FIGS. 4-6 illustrate example neuronal networks and the associated nodes to be ablated by the system of FIG. 1.
Figure 5:
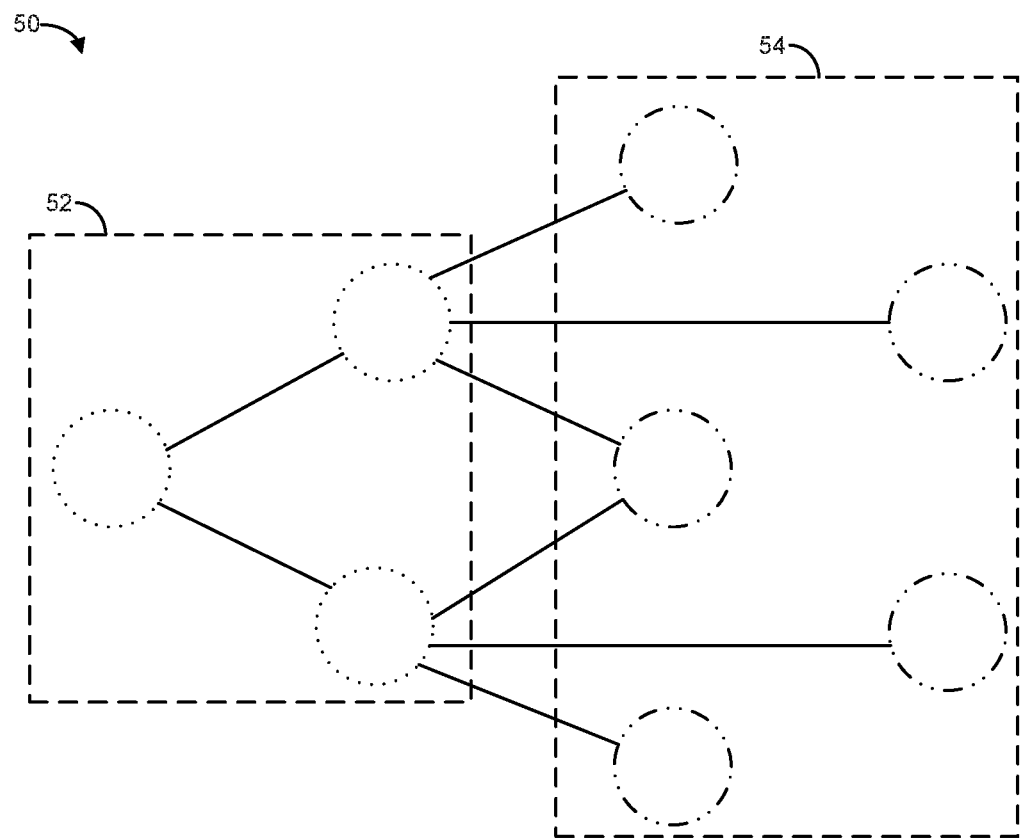
Figure 6:
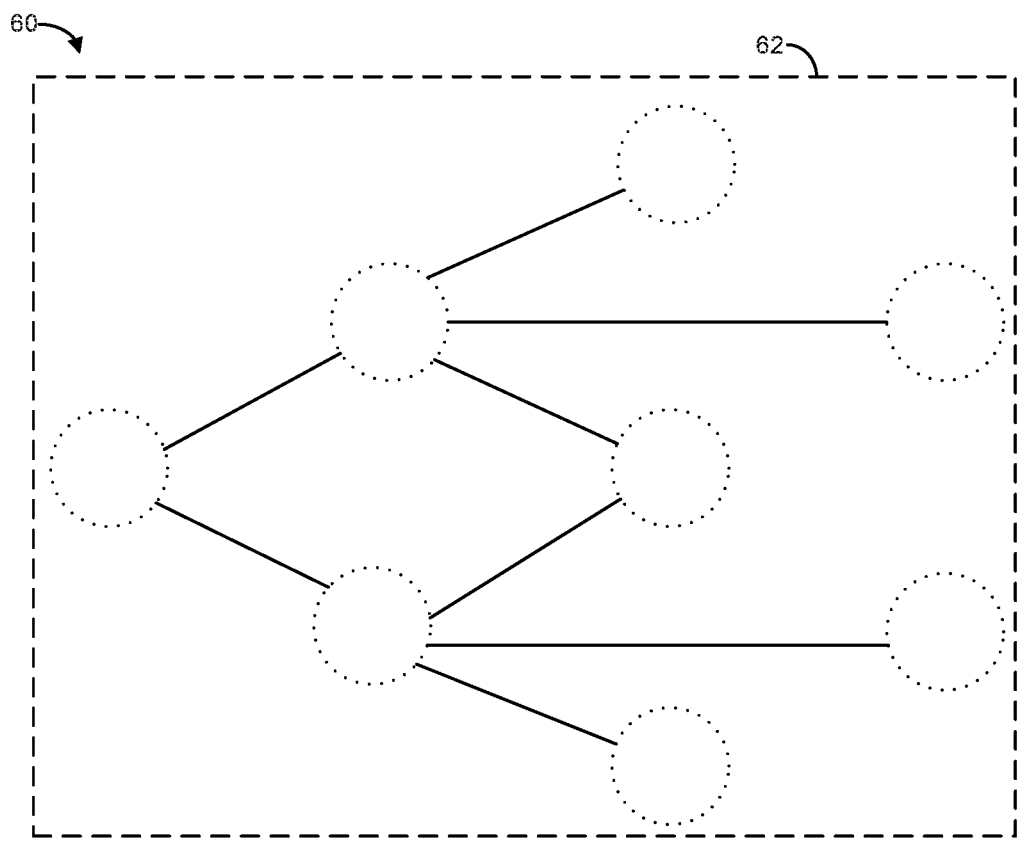

As an example, the electrode 24 can be used in the navigation process, specifically in the fine adjustment. The coarse coordinates can be determined based on data stored in the non-transitory memory 16. For example, the data can include conduction data that can be used to provide clinical and computational analyses (that can include frequency and centrality analyses) to determine a zone of activity (e.g., shown in FIGS. 4-6) that is responsible for a primary organization of an abnormal brain activity contributing to the neurological condition. Notably, FIGS. 4-6 show an example taking place in the brain; similar conduction maps can be created for the spinal cord or peripheral nervous system.

Based on the conduction data, a portion of the zone of activity (or neural network) that is responsible for a primary organization of the abnormal brain activity can be localized by the computer 14. FIGS. 4-6 show example zones of activity that can be identified by the computing device 14. In FIG. 4, the conduction map 40 indicates that the zone of activity 42 includes a single node, the zone that propagates the abnormal brain activity 44 includes two nodes, and the unaffected zone 46 includes five nodes. Accordingly, the area of ablation can include the one node of the zone of activity 42. In FIG. 5, the conduction map 50 indicates that the zone of activity 52 includes three nodes, and the zone that propagates the abnormal brain activity 54 includes five nodes. Therefore, the area of ablation can include the three nodes of the zone of activity 52. In FIG. 6, the conduction map 60 indicates that the zone of activity 62 includes eight nodes, and the area of ablation can include all eight nodes in the zone of activity 62.

When the probe 12 reaches the coarse location determined by the computing device 14, the electrode 24 can provide feedback that the computing device 14 can use to determine the fine location for delivery of the lesion. Upon formation of the lesion, the computing device 14 can determine when conduction is reduced or stopped because of the lesion. In some instances, a second lesion can be placed by the same or different one of the contacts in a same or different area so that the abnormal conduction is reduced or eliminated.

IV. Methods

Figure 7:
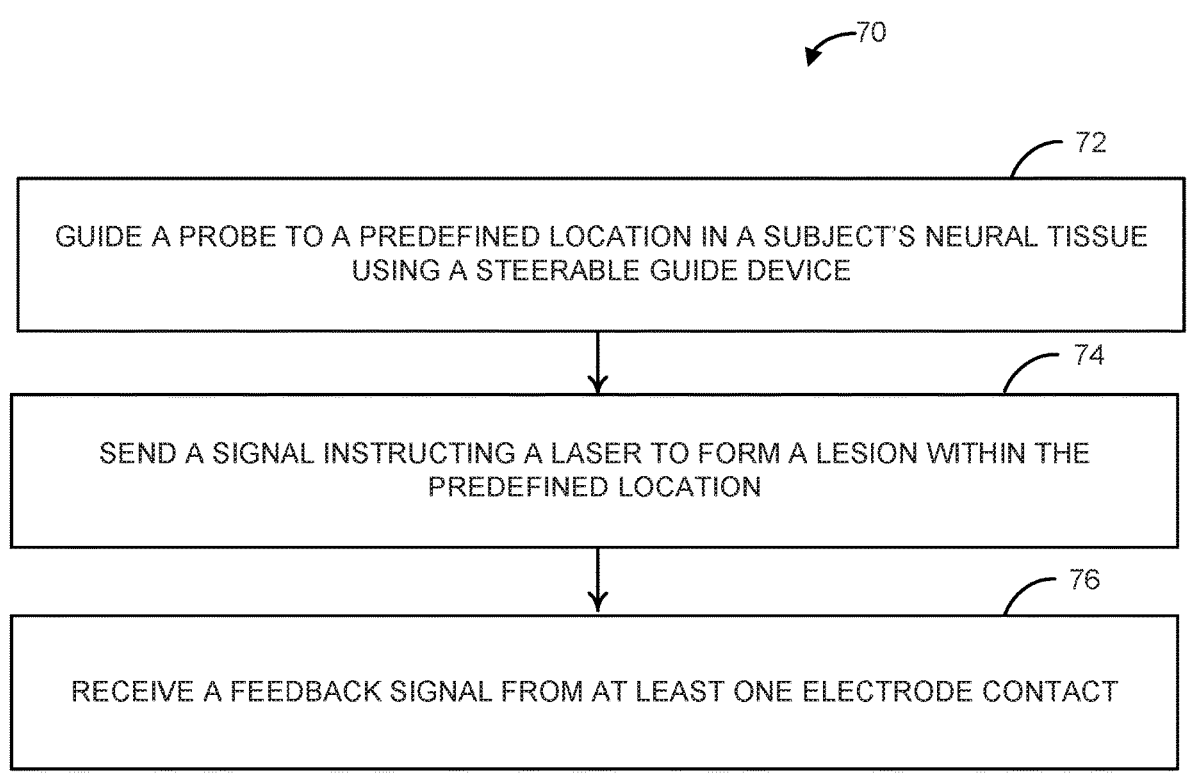
FIGS. 7 and 8 are process flow diagrams illustrating methods for creating a lesion in the patient's neural tissue to treat a neurological condition in accordance with another aspect of the present disclosure.
Figure 8:
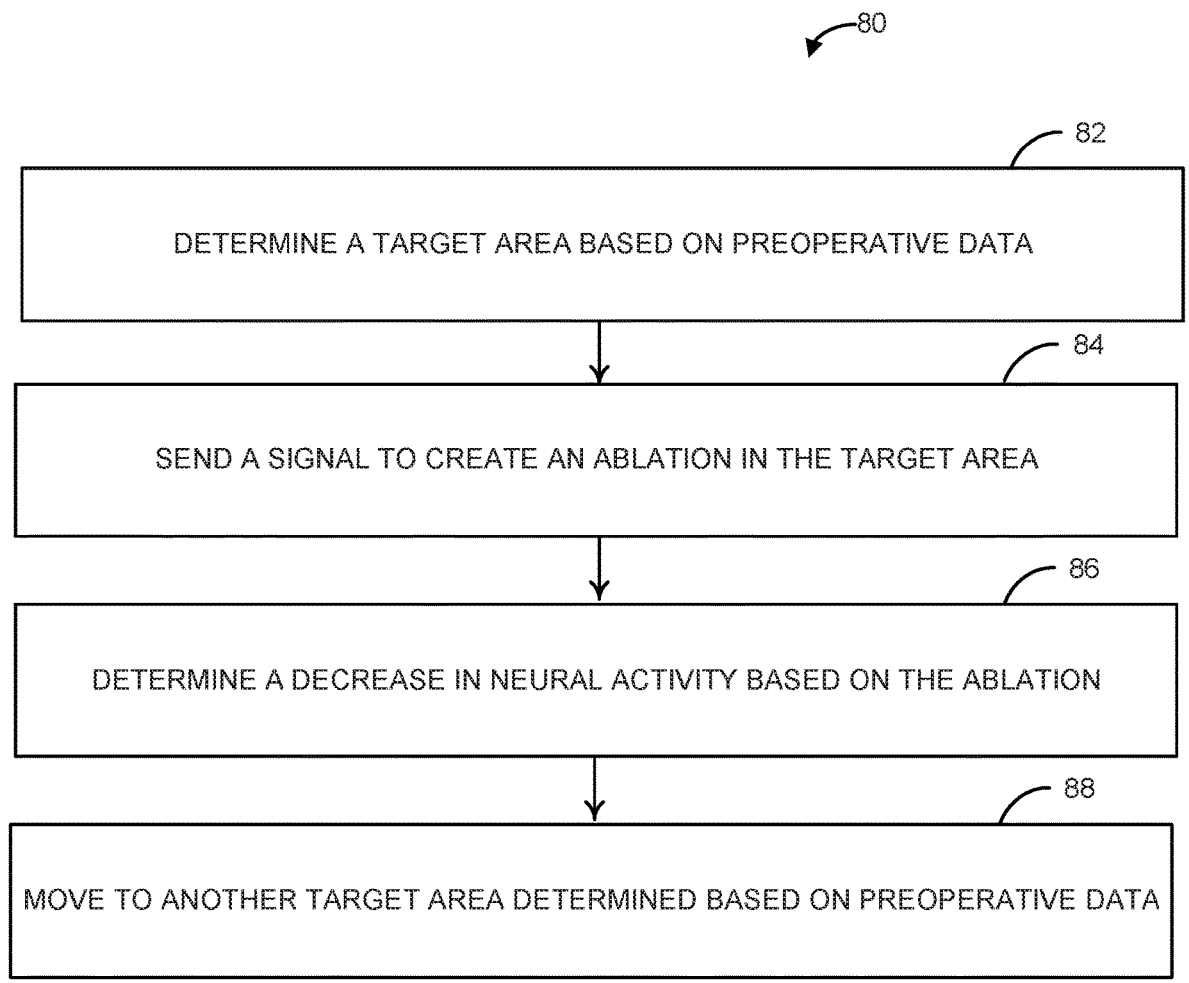

Another aspect of the present disclosure can include methods 70 and 80 for creating a lesion in a patient's neural tissue to treat a neurological condition, such as epilepsy, brain tumor, psychiatric disorder, movement disorder, chronic pain, cancer pain, or the like, as shown in FIGS. 7 and 8. For example, the lesion can be permanent to stop conduction in the area of the one or more lesions. In other instances, the lesion can be temporary, made for testing in advance of a permanent ablation of the area to temporarily cease local nerve activity to determine if there is a deficit (e.g., speech, motor, etc.) in advance of a permanent ablation. For example, the temporary lesion can be fully reversible so that normal neural activity can resume at the spot of the temporary lesion. In some instances, the temporary lesion can be created by reducing the temperature of a probe to a sub-lethal level at the location of the temporary lesion. After the temporary lesion is formed, tests can be performed to determine whether the temporary lesion stops the abnormal neural activity based on an electro-clinical analysis (e.g., SEEG). If the temporary lesion does stop the abnormal brain activity, a permanent lesion can be created. However, if the temporary lesion does not stop the abnormal neural activity, the temporary lesion can return to normal and another temporary lesion can be created. The temporary lesion can last from minutes to several days. As an example, the methods 70 and 80 can be accomplished using the system 10 as shown in FIG. 1.

The methods 70 and 80 are illustrated as process flow diagrams with flowchart illustrations. For purposes of simplicity, the methods 70 and 80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 70 and 80.

FIG. 7 illustrates a method 70 for creating a lesion in a patient's neural tissue to treat a neurological condition. In some instances, the method 70 can be performed using a probe 12, like the steerable hybrid catheter (SHC) shown in FIG. 3, that includes a laser device 22 to create a lesion in a portion of neurological tissue; an electrode 24 that includes at least one electrode contact to detect progressive vanishing of neural activity from the portion of neurological tissue due to the lesion; and a steerable guide device 26 to guide the probe to the portion of neurological tissue to create the lesion. The steps of method 70 can be performed by computing device 14 of FIG. 1.

At 72, the probe can be guided to a predefined location in a subject's portion of neural tissue using the steerable guide device. In some instances, the steerable guide device can be flexible (e.g., a steerable guide wire or an inflatable balloon) that can be housed a side port of the SHC and able to be inserted into the neural tissue to guide the probe to the portion of neural tissue. In some instances, the steerable guide device can be guided to the portion by a navigation system (e.g., computer or manual based on a fluoroscopic image). The portion of neural tissue can be predetermined based on pre-operative electrical conduction data recorded non-invasively (e.g., recorded with a mapping technique, such as a stereo-electroencephalography mapping procedure). Upon reaching the preliminary location, the probe can be guided more finely to the location to create the lesion based on feedback from one or more electrode contacts within the probe.

At 74, a signal instructing a laser of the probe to form a lesion within the predefined location (e.g., at the fine location). The lesion can be formed by applying ablative energy to the portion of neural tissue. In some instances, the ablative energy can be due to a small amount of ablative current being passed through the laser device. In other instances, the ablative energy can be due to a high intensity laser light, heating, or cooling produced by the laser device. The lesion can be small, but strategically located in a predetermined zone of activity determined based on conduction data (either recorded before the ablation or updated by feedback during the ablation). Multiple lesions can be created (and the process repeated multiple time) until the abnormal neural activity is completely extinguished.

At 76, a feedback signal can be received from at least one electrode contact. The feedback signal can be indicative of whether the ablative energy should increase or decrease. For example, the computing device can receive the feedback and determine whether the abnormal neural activity is extinguished in the portion of neural tissue based on the feedback. In circumstances when the feedback indicates that the abnormal neural activity in the portion of neural tissue has ended, the laser device can decrease or end the ablation. In cases when the feedback indicates that the abnormal neural activity in the portion of the neural tissue has not ended, the laser device can increase the ablation (e.g., to a wider area in the portion of neural tissue) or continue ablating the portion of neural tissue at the same intensity.

A method 80 is shown in FIG. 8, in which abnormal neural activity is extinguished in a patient's neural tissue. At 82, a target area (at least one area in the patient's neural tissue responsible for abnormal neural activity) can be determined. This determination can be based on conduction data recorded pre-operatively using electrodes that are placed at pre-determined non-invasive and/or invasive locations. For example, the conduction data recorded by the plurality of electrodes can be used to provide clinical and computational analyses (that can include frequency and centrality analyses) to determine a zone of activity (e.g., shown in FIGS. 4-6) that is responsible for a primary organization of an abnormal neural activity contributing to the neurological condition.

Based on the zone of activity, a location for lesion formation can be determined. A probe can be guided to the location, and at 74, a signal can be sent to the probe to create an ablation in the target area. For example, ablative energy (e.g., an electric current burst or a burst of laser light) can be delivered to the area by the laser device of the probe. At 76, a decrease in neural activity due to the lesion is determined. As the lesion is created, one or more electrode contacts of the probe can send a signal to determine a decrease in the abnormal neural activity associated with the formation of the lesion. The computer can determine the progressive vanishing of the abnormal neural activity corresponding to the neurological condition due to the lesion. At 88, the steerable guide device of the probe can move the probe to another area in the patient's neural tissue responsible for abnormal neural activity and repeat the method 80 at the another area.

From the above description, those skilled in the art will perceive improvements, changes and modifications. Such improvements, changes and modifications are within the skill of one in the art and are intended to be covered by the appended claims.

What is claimed is:
1. A system comprising:
 a steerable hybrid catheter device configured to be implanted within a subject's central nervous system tissue, the steerable hybrid catheter device comprising:
  a catheter comprising:
   a laser device; and
   an electrode comprising at least one contact configured for recording an electrical signal indicative of neural activity; and
  a steerable device insertable within a side port of the catheter; and
 a computing device coupled to the steerable hybrid catheter comprising:
  a non-transitory memory storing instructions; and
  a processor configured to access the non-transitory memory and execute the instructions to:
   instruct the steerable device to guide the catheter to a predetermined location within the subject's central nervous system tissue, wherein the predetermined location is determined based on pre-operative electrical data from the subject's central nervous system tissue;
   deliver a signal to the laser device that causes the laser device to form a lesion within the predetermined location; and
   receive a feedback signal from the at least one contact, the feedback signal comprising an electrical signal of neural activity in the predetermined location indicative of progress of the lesion.

2. The system of claim 1, wherein the steerable device is configured to guide the steerable hybrid catheter to the predetermined location within a three-dimensional space, wherein the determined location corresponds to a portion of a specific neuronal network.

3. The system of claim 1, wherein the pre-operative electrical data is recorded during a stereo-electroencephalography mapping procedure.

4. The system of claim 1, wherein the laser device is configured to deliver a pulse of high energy to the predetermined location to create the lesion in the predetermined location.

5. The system of claim 1, wherein the laser device is configured to deliver a pulse of light or current to create the lesion.

6. The system of claim 1, wherein the at least one contact is further configured for stimulation.

7. The system of claim 1, wherein the steerable device comprises a guidewire or an inflatable balloon.

* * * * *